United States Patent [19]

Götschi et al.

[11] Patent Number: 4,619,787

[45] Date of Patent: Oct. 28, 1986

[54] BETA LACTAMS

[75] Inventors: Erwin Götschi, Reinach, Switzerland; Christian Hubschwerlen, Durmenach, France

[73] Assignee: Hoffmann-La Roche Inc., Nutley, N.J.

[21] Appl. No.: 670,796

[22] Filed: Nov. 13, 1984

[30] Foreign Application Priority Data

Nov. 23, 1983 [CH] Switzerland ............... 6286/83

[51] Int. Cl.[4] .................. C07D 405/04; C07F 7/10
[52] U.S. Cl. ............................ 540/200; 540/351
[58] Field of Search .................. 260/330.9, 245.2 T

[56] References Cited

FOREIGN PATENT DOCUMENTS 73061  3/1983  European Pat. Off. .
78026  5/1983  European Pat. Off. .

OTHER PUBLICATIONS

Hiroshi Matsunaga, et al., "Enantioselective Synthesis . . .", Tetrahedron Letters, vol. 24, No. 29 (1983).
Robert M. Adlington et al., J. Chem. Soc. Perkin Trans. I (1983), pp. 605–611.
T. Kametani et al., J. Org. Chem. (1982), vol. 47, pp. 2328–2331.
Hubschwerlen et al., Helvetica Chimica Acta, vol. 66(7) (1983), pp. 2206–2209.

*Primary Examiner*—Norma S. Milestone
*Attorney, Agent, or Firm*—Jon S. Saxe; Bernard S. Leon; George W. Johnston

[57] ABSTRACT

The novel compounds of the formula wherein
$R^1$ is hydrogen, a residue readily removable by reduction, lower 1-hydroxyalkyl or lower alkanoyl and $R^2$ is hydrogen, or each of $R^1$ and $R^2$ is a residue readily removable by reduction;
$R^3$ is hydrogen or lower alkyl;
$R^4$ is hydrogen or a readily removable protecting group; and
A is lower alkylidene or ($C_{5-7}$)-cycloalkylidene, are valuable intermediates for the manufacture of antimicrobially-active β-lactams.

2 Claims, No Drawings

BETA LACTAMS

BACKGROUND OF THE INVENTION

This invention relates to beta-lactam intermediates.

SUMMARY OF THE INVENTION

The present invention is concerned with optically uniform beta-lactams of the formula

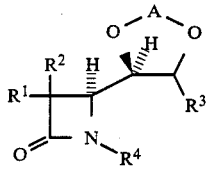

wherein
- $R^1$ is hydrogen, a residue readily removable by reduction, lower 1-hydroxyalkyl or lower alkanoyl and $R^2$ is hydrogen, or each of $R^1$ and $R^2$ is a residue readily removable by reduction;
- $R^3$ is hydrogen or lower alkyl;
- $R^4$ is hydrogen or a readily removable protecting group; and
- A is lower alkylidene or $(C_{5\text{-}7})$-cycloalkylidene.

The compounds of formula I are valuable intermediates for the manufacture of antimicrobially active beta-lactams, such as (+)-thienamycin.

DETAILED DESCRIPTION OF THE INVENTION

The present invention is concerned with optically uniform β-lactams of the formula

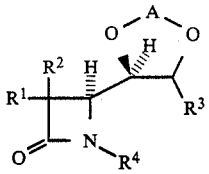

wherein
- $R^1$ is hydrogen, a residue readily removable by reduction, lower 1-hydroxyalkyl or lower alkanoyl and $R^2$ is hydrogen, or each of $R^1$ and $R^2$ is a residue readily removable by reduction;
- $R^3$ is hydrogen or lower alkyl;
- $R^4$ is hydrogen or a readily removable protecting group; and
- A is lower alkylidene or $(C_{5\text{-}7})$-cycloalkylidene.

As used herein, the term "hydrocarbon group" or "hydrocarbon residue" denotes any saturated or unsaturated straight-chain, branched, cyclic or aromatic radical (e.g., alkyl, alkenyl, alkynyl, aryl, cycloalkyl).

The term "alkyl" or "alkane" denotes straight or branched chain saturated aliphatic hydrocarbon groups: (e.g., methyl, ethyl, isopropyl, n-butyl, s-butyl, t-butyl, octyl).

The term "lower alkyl" as well as other groups in the specification containing the term "lower" denotes residues and compounds containing 1 to 4 carbon atoms.

The term "alkylidene" denotes alkyl groups with 2 free valences on the same carbon atom (e.g., ethylidene, isopropylidene, butylidene).

The term "alkanoyl" denotes moieties derived from alkanecarboxylic acid moieties (e.g., formyl, acetyl, propionyl, etc.)

The term "alkoxy" denotes an alkyl group containing an oxygen atom. (e.g., methoxy, ethoxy, isopropoxy, etc.)

The term ("$C_{5\text{-}7}$)-cycloalkylidene" denotes cyclic hydrocarbon residues containing from 5 to 7 carbon atoms and 2 free valencies on the same carbon atom (e.g., cyclohexylidene).

The term "halogen" includes all four halogens, i.e., fluorine, chlorine, bromine and iodine.

The term "lower 2-alkenyl" denotes an olefinic hydrocarbon group which can be straight-chain or branched, which has a double bond in the 2-position and which contains from 3 to 4 carbon atoms (e.g., 2-propenyl(allyl), 2-methallyl, 2-butenyl).

The term "aryl" signifies a mononuclear or a polynuclear aromatic hydrocarbon group which is unsubstituted or substituted in one or more positions with lower alkylenedioxy, halogen, nitro, a lower alkyl or lower alkoxy. The preferred aryl groups are the substituted and unsubstituted mononuclear aryl groups. Suitable aryl groups are unsubstituted or substituted phenyl, napthyl, anthryl and phenanthryl.

The term "residue readily removable by reduction" denotes any conventional radical that can be reductively removed from a lactam ring and replaced by hydrogen. Residues readily removable by reduction include halogen (i.e., chlorine, bromine and iodine), lower alkylthio groups, lower alkylsulphonyloxy groups (e.g., methylsulphonyloxy) and arylsulphonyloxy groups (i.e. phenylsulphonyloxy groups unsubstituted or substituted by lower alkyl, halogen and the like (e.g., benzenesulphonyloxy- and p-toluenesulphonyloxy). Preferred residues readily removable by reduction are the aforementioned halogens, especially chlorine.

The term "a readily removable protecting group" denotes any conventional amino protecting group. These are any conventional radical utilized to protect an amide. Readily removable protecting groups include unsubstituted or lower alkoxy-substituted phenyl; unsubstituted 1-phenyl lower alkyl; a 1-phenyl lower alkyl group substituted with lower alkoxy on the phenyl ring; lower 2-alkenyl; tri(lower alkyl)silyl and the like.

In the pictorial representations of the compound of this application, a solid tapering line indicates a substituent which in the beta-orientation (above the plane of the molecule) and a series of parallel lines indicates a substituent which is in the alpha orientation (below the plane of the molecule).

The term "optically uniform" denotes that the compounds so designated have the absolute configuration shown in formula I.

Preferred compounds of formula I are those in which $R^1$ signifies hydrogen or 1-hydroxyethyl and $R^2$ signifies hydrogen. $R^3$ preferably signifies hydrogen, and A preferably signifies lower alkylidene. $R^4$ preferably signifies hydrogen, 2,4-dimethoxybenzyl, 3,4-dimethoxybenzyl, 4-methoxybenzyl or t-butyldimethylsilyl.

Especially preferred compounds of formula I in the scope of the present invention are:
(3S,4S)-1-(2,4-dimethoxydbenzyl)-4-[(R)-2,2-dimethyl-1,3-dioxolan-4-yl]-3-[(R)-1-hydroxyethyl]-2-azetidinone, (3S,4S)-1-(t-butyldimethylsilyl)-4-[(R)-2,2-dimethyl-1,3-dioxolan-4-yl]-3-[(R)-1-hydroxyethyl]-2-azetidinone, (S)-1-(2,4-dimethoxybenzyl)-4-[(R)-2,2-dimethyl-1,3-dioxolan-4-yl]-2-azetidinone, (S)-1-(t-butyldimethylsilyl)-4-[(R)-2,2-dimethyl-1,3-dioxolan-4-yl]-2-azetidinone and (S)-4-[(R)-2,2-dimethyl-1,3-dioxolan-4-yl]-2-azetidinone.

The compounds of formula I can be manufactured in accordance with the invention by reacting a reactive derivative of a carboxylic acid of the formula

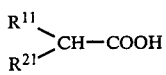

wherein
$R^{11}$ signifies a residue readily removable by reduction and
$R^{21}$ signifies hydrogen or a residue readily removable by reduction,
in the presence of a base with a compound of the formula

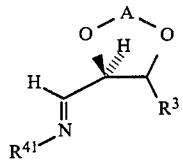

wherein
$R^{41}$ signifies a readily removable protecting group and
$R^3$ and A have the significance given above,
if desired reducing a compound of formula I obtained in which $R^1$ signifies a residue readily removable by reduction, $R^2$ signifies hydrogen or a residue readily removable by reduction and $R^4$ signifies a readily removable protecting group and $R^3$ and A have the significance given above and previously or subsequently removing the protecting group, or reacting a compound of formula I obtained in which $R^1$ and $R^2$ signify hydrogen and $R^3$, $R^4$ and A have the significance given above in the presence of a strong base with a lower aldehyde or a reactive derivative of a lower fatty acid, whereby, if desired, the lactam nitrogen atom is previously blocked with a readily removable protecting group when $R^4$ signifies hydrogen, and subsequently removing the protecting group, or reducing the lower alkanoyl group in a compound of formula I obtained in which $R^1$ signifies lower alkanoyl and $R^2$ signifies hydrogen and $R^3$, $R^4$ and A have the significance given above and subsequently removing a protecting group which may be present.

The reaction of a reactive derivative of a carboxylic acid of formula II with a compound of formula III is a cyclocondensation which is known and familiar to a person skilled in the art. Suitable reactive carboxylic acid derivatives of compounds of formula II in which $R^{11}$ signifies a residue readily removable by reduction and $R^{21}$ signifies hydrogen or a residue readily removable by reduction are, for example, the corresponding carboxylic acid halides, especially the carboxylic acid chlorides, corresponding carboxylic acid anhydrides and mixed anhydrides (e.g. with trifluoroacetic acid, aromatic sulphonic acids and the like), corresponding carboxylic acid imidazolides and the like. In this case the reaction is conveniently carried out in the presence of a base, for example a tertiary amine such as triethylamine, and in an inert organic solvent, whereby ethers such as tetrahydrofuran, diethyl ether, t-butyl methyl ether, dioxan, ethylene glycol dimethyl ether or the like, halogenated hydrocarbons such as methylene chloride, chloroform, 1,2-dichloroethane or the like, toluene, acetonitrile, dimethylformamide or the like especially come into consideration. The above cyclocondensation is carried out in a temperature range of about $-78°$ C. to about 80° C.

The above reaction of a compound of formula II with the optical uniform compound of formula III yields a correspondingly substituted compound of formula I above having the stereochemistry shown in formula I. It has been found that the use of the optically active compound of formula III in the above cyclocondensation yields the desired compound in high optical yield.

The reduction of a compound of formula I obtained in which $R^1$ signifies a residue readily removable by reduction and $R^2$ signifies hydrogen or a residue readily removable by reduction to give a compound of formula I in which $R^1$ and $R^2$ each signify hydrogen can be carried out according to methods which are known per se and which are familiar to any person skilled in the art. An especially suitable method for the reductive removal of halogen atoms is catalytic hydrogenation in the presence of catalysts such as palladium/carbon or Raney-nickel and in the presence of an acid-binding agent such as potassium hydroxide. In this case a lower alcohol such as methanol is preferably used as the solvent. Depending on the reactivity of the compound used the reduction is carried out at a hydrogen pressure from normal pressure to about 100 bar and in a temperature range of about 0° C. to about 100° C.

The reaction of a compound of formula I in which $R^1$ and $R^2$ signify hydrogen with a lower aldehyde or a reactive derivative of a lower fatty acid in the presence of a strong base gives a compound of formula I in which $R^1$ signifies lower 1-hydroxyalkyl or lower alkanoyl and $R^2$ signifies hydrogen. This is also a reaction which is familiar to the person skilled in the art. For example, a compound of formula I in which $R^1$, $R^2$ and $R^4$ signify hydrogen can be converted with an alkyl lithium such as butyl lithium into the corresponding dilithium salt and this can be treated with acetaldehyde or a reactive acetic acid derivative such as methyl acetate. This reaction is preferably carried out under a protective gas, e.g. nitrogen or argon, in an inert solvent such as tetrahydrofuran and at a temperature between $-80°$ and 50° C. Alternatively, a compound of formula I in which $R^1$ and $R^2$ signify hydrogen and $R^4$ signifies a readily removable protecting group can be converted with a lithium amide such as lithium diisopropylamide into the corresponding monolithium salt and this can be treated with acetaldehyde or a reactive acetic acid derivative such as methyl acetate under a protective gas, in an inert solvent such as tetrahydrofuran and at a temperature of $-80°$ C. to $-50°$ C. Finally, a compound of formula I in which $R^1$, $R^2$ and $R^4$ signify hydrogen can firstly be blocked at the lactam nitrogen atom by the introduction of a readily removable protecting group and then 1-hydroxyalkylated or alkanoylated as previously described. The introduction of a protecting group is carried out in a manner known per se, for example by reacting a corresponding compound of formula I with a 1-phenyl-lower alkyl halide, 1-phenyl-lower alkyl-lower alkylsulphonate or 1-phenyl-lower alkyl-arylsulphonate optionally substituted on the phenyl ring or a tri(lower alkyl)halosilane in an inert solvent such as dimethylformamide and in the presence of an acid-binding agent, e.g. a tertiary amine such as triethylamine. The reaction temperature conveniently lies in a range of about 0° C. to room temperature.

The reduction of a compound of formula I in which $R^1$ signifies lower alkanoyl and $R^2$ signifies hydrogen to give a compound of formula I in which $R^1$ signifies lower 1-hydroxyalkyl and $R^2$ signifies hydrogen can also be carried out according to methods which are known per se and which are familiar to any person skilled in the art. Suitable reducing agents are, for example, metal borohydrides such as sodium borohydride and potassium tris-sec.-butylborohydride, whereby the solvents and reaction conditions which are usual in the case of such reductions are used. However, the reduction can also be carried out by means of catalytic hydrogenation on platinium catalysts at room temperature (about 23° C.) and normal pressure (about 1 atm.) in a solvent such as ethyl acetate or methanol.

Finally, the removal of N-protecting groups which may be present in the compounds of formula I can also be carried out according to methods which are known per se and which are familiar to any person skilled in the art. The 2,4-dimethoxybenzyl group can be removed, for example, by treating a correspondingly protected compound of formula I with potassium persulphate in aqueous acetonitrile at an elevated temperature.

The compounds of formula I are valuable intermediates for the manufacture of antimicrobially-active β-lactams. For example, they can be converted into (+)-thienamycin according to the following Reaction Scheme:

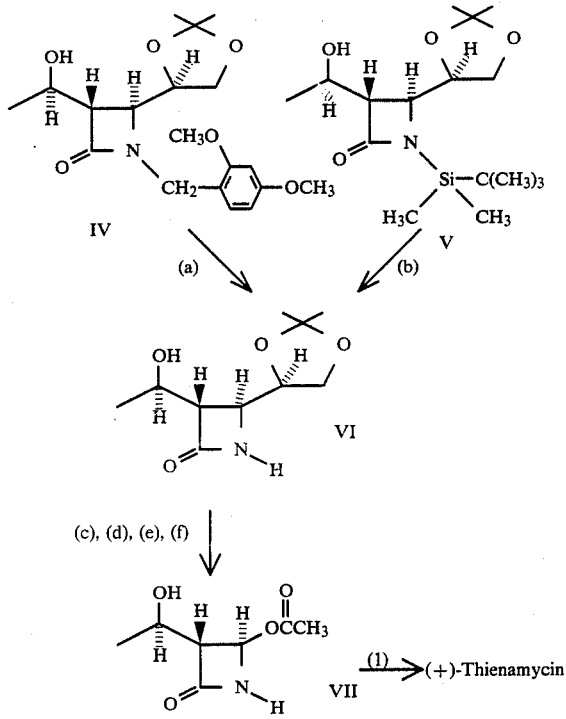

(a) $K_2S_2O_8/CH_3CN/H_2O$;
(b) $NH_4F/MeOH$;
(c) p-TsOH/MeOH/$H_2O$;
(d) $NaIO_4/MeOH/H_2O$;
(e) $Ag_2O/H_2O$;
(f) $Pb(OAc)_4/DMF/HOAc$.
(1) European Patent Publication No. 78,026.
J. Amer. Chem. Soc. 103, 6765 (1981).

The compound of formula VI can be manufactured by removing the 2,4-dimethoxybenzyl protecting group from the compound of formula IV what can be achieved by using standard methods, e.g. by treatment with potassium persulfate in a mixture of acetonitrile and water in a temperature range between 50° C. and 100° C. at a pH between 3 and 7 (step a).

The compound of formula VI can also be obtained by treating the compound of formula V with 0.1 to 1 equivalent of ammonium fluoride in methanol at room temperature (step b). The transformation of the acetonitrile of formula VI into the acetate of formula VII can be achieved by a reaction sequence which comprises the hydrolysis of the acetonide function, e.g. by treating the compound of formula VI for 2 to 20 hours at 20° C. to 70° C. with a catalytic amount of p-toluenesulfonic acid in a mixture of water and methanol (step c), oxidative cleavage of the resulting diol by treatment with 1 equivalent of sodium(meta)periodate in the same solvent system at 0° C. to 20° C. (step d), oxidation of the resulting aldehyde to the corresponding carboxylic acid, e.g. with silver(I)oxide in a diluted aqueous sodium hydroxide solution at 0° C. (step e), and, finally, oxidative decarboxylation of this acid, e.g. with lead tetraacetate in a mixture of N,N-dimethylformamide and acetic acid at a temperature of 30° C. to 40° C. (step f).

The transformation of the compound of formula VII into (+)-thienamycin has been described in European Pat. Publication No. 78,026.

The following Examples illustrate the invention. Unless otherwise stated, temperatures are in degrees Celsius, normal pressure is about 1 atmosphere and room temperature is about 23° C. Unless indicated otherwise, the Examples were carried out as written.

EXAMPLE 1

(a) To a solution, stirred at room temperature, of 12.3 g (95.0 mmol) of 2,3-O-isopropylidene-L-glyceraldehyde in 100 ml of dry methylene chloride (free from methanol) are added 10 g of molecular sieve 4A and subsequently dropwise a solution of 15.86 g (95 mmol) of 2,4-dimethoxybenzylamine in 20 ml of dry methylene chloride. The reaction mixture is stirred at room temperature for 2 hours, subsequently treated with 5 g of anhydrous magnesium sulphate, stirred for a further 30 minutes and subsequently filtered, whereby the filter cake is washed with 20 ml of methylene chloride.

(b) The organic solution of isopropylidene-L-glyceraldehyde (2,4-dimethoxybenzyl)imine obtained is cooled to −5° under argon and treated while stirring with 17.2 ml (95 mmol) of triethylamine. After a few minutes there is added thereto over a period of 1 hour a solution of 7.9 ml (73.4 mmol) of chloroacetyl chloride in 100 ml of dry methylene chloride, the reaction mixture is stirred at −5° for 2 hours and subsequently left to warm to room temperature. The reaction mixture is stirred at room temperature overnight, washed three times with 100 ml of water each time and with 100 ml of sodium chloride solution and the solution obtained is dried over sodium sulphate. The dried solution is evaporated and the residue is crystallized from ethyl acetate. After recrystallization from ethyl acetate there is obtained (3S,4R)-3-chloro-1-(2,4-dimethoxybenzyl)-4-[(R)-2,2-dimethyl-1,3-dioxolan-4-yl]-2-azetidinone as colourless crystals of melting point 140°–142°; $[\alpha]_D^{20} = +33.2°$ (c=1, chloroform).

EXAMPLE 2

A solution of 4.26 g (12.0 mmol) of (3S,4R)-3-chloro-1-(2,4-dimethoxybenzyl)-4-[(R)-2,2-dimethyl-1,3-dioxolan-4-yl]-2-azetidinone and 3 g (53 mmol) of potassium hydroxide in 50 ml of methanol is hydrogenated in the presence of 400 mg of 5 percent palladium/carbon for 1 hour at normal pressure. The catalyst is filtered off, the filtrate is diluted with ethyl acetate and washed with 1M phosphate buffer (pH 7) and saturated sodium chloride solution. The organic phase is dried over sodium sulphate and evaporated, whereupon the residue is chromatographed on silica gel with ethyl acetate/hexane as the eluent. After two-fold crystallization from methylene chloride/hexane there is obtained (S)-1-(2,4-dimethoxybenzyl)-4-[(R)-2,2-dimethyl-1,3-dioxolan-4-yl]-2-azetidinone as white crystals of melting point 85°–86°; $[\alpha]_D^{20} = +50.3°$ (c=1, chloroform).

EXAMPLE 3

0.65 ml of a 1.7M solution of butyl lithium in hexane is added to a solution, cooled to −65°, of 111 mg (1.1 mmol) of diisopropylamine in 4 ml of tetrahydrofuran. The mixture is cooled to −78° and treated after 15 minutes with a solution of 321 mg (1 mmol) of (S)-1-(2,4-dimethoxy-benzyl)-4-[(R)-2,2-dimethyl-1,3-dioxolan-4-yl]-2-azetidinone in 1 ml of tetrahydrofuran. The mixture is stirred at −78° for 45 minutes and then a solution of 100 mg (2,27 mmol) of acetaldehyde in 0.5 ml of tetrahydrofuran is added dropwise within 3 minutes thereto, whereby the temperature rises to −70°. The mixture is stirred for 10 minutes, the cooling bath is removed, the reaction solution is treated with 2 ml of 14 percent aqueous ammonium chloride solution and extracted with 30 ml of ethyl acetate. The organic phase is washed with saturated sodium chloride solution, dried over sodium sulphate and evaporated in vacuo. The residue is chromatographed on 10 g of silica gel with ethyl acetate/hexane (2:1) as the eluent. There is obtained (3S,4S)-1-(2,4-dimethoxybenzyl)-4-[(R)-2,2-dimethyl-1,3-dioxolan-4-yl]-3-[(R)-1-hydroxyethyl]-2-azetidinone which is obtained as fine needles of melting point 145°–146° after crystallization from ethyl acetate/hexane.

EXAMPLE 4

A solution of 1.47 g (5.45 mmol) of potassium persulphate in 25 ml of water is added dropwise within 30 minutes to a suspension, heated to 80°, of 0.964 g (3 mmol) of (S)-1-(2,4-dimethoxybenzyl)-4-[(R)-2,2-dimethyl-1,3-dioxolan-4-yl]-2-azetidinone in a mixture of 10 ml of water and 10 ml of acetonitrile, whereby the pH of the reaction mixture is held at 5 by the addition of saturated sodium hydrogen carbonate solution. The reaction mixture is stirred for a further 1 hour at pH 5, then cooled and extracted three times with 50 ml of methylene chloride each time. The organic phases are washed with 20 ml of saturated sodium chloride solution, dried over sodium sulphate and evaporated. The residue is chromatographed on silica gel with ethyl acetate/hexane (3:1 by volume) as the eluent. By crystallization of the resulting material from ethyl acetate/hexane there is obtained (S)-4-[(R)-2,2-dimethyl-1,3-dioxolan-4-yl]-2-azetidinone as white crystals of melting point 91°–92°; $[\alpha]_D^{20} = +13.6°$ (c=1, ethyl acetate).

EXAMPLE 5

A solution, cooled to 0°, of 17.1 g (0.1 mmol) of (S)-4-[(R)-2,2-dimethyl-1,3-dioxolan-4-yl]-2-azetidinone and 15.1 g (0.1 mol of t-butyldimethylchlorosilane in 100 ml of dimethylformamide is treated while stirring with 10.6 g (0.105 mol) of triethylamine, whereby a precipitate results immediately. The mixture is stirred at 0° for 2 hours, then diluted with 200 ml of ether and the reaction mixture is washed five times with 80 ml of water each time. The aqueous phases are then extracted with 100 ml of ether. The organic phases are dried over sodium sulphate and evaporated, whereupon the residual oil is distilled. There is obtained (S)-1-(t-butyldimethylsilyl)-4-[(R)-2,2-dimethyl-1,3-dioxolan-4-yl]-2-azetidinone of boiling point 84°–87° (0.5 Torr); $[\alpha]_D^{20} = -22.7°$ (c=1, ethyl acetate).

EXAMPLE 6

16.2 ml of a 1.7M solution of butyl lithium in hexane is added dropwise within 5 minutes to a solution (cooled to −65°) of 2.78 g (27.5 mmol) of diisopropylamine in 100 ml of tetrahydrofuran. The resulting mixture is then cooled to −76° and treated after 15 minutes with a solution of 7.14 g (25 mmol) of (S)-1-(t-butyldimethylsilyl)-4-[(R)-2,2-dimethyl-1,3-dioxolan-4-yl]-2-azetidinone in 6 ml of tetrahydrofuran. The mixture is stirred at −76° for 30 minutes and then a solution of 2.65 g of acetaldehyde in 5 ml of tetrahydrofuran is added dropwise within 10 minutes thereto. The mixture is stirred for 15 minutes, the cooling bath is removed, the reaction solution is treated with 20 ml of 14 percent (by volume) aqueous ammonium chloride solution and extracted with 100 ml of ethyl acetate. The organic phase is washed with saturated sodium chloride solution, dried over sodium sulphate and evaporated in vacuo. The residual oil is taken up in 10 ml of hexane and the solution is left to stand at −20°. Colourless crystals of melting point 80°–90° are obtained. After repeated recrystallization from ethyl acetate/hexane there is obtained (3S,4S)-1-(t-butyldimethylsilyl)-4-[(R)-2,2-dimethyl-1,3-dioxolan-4-yl]-3-[(R)-1-hydroxyethyl]-2-azetidinone of melting point 95°–96°; $[\alpha]_D^{20} = 16.6°$ (c=1, ethyl acetate).

We claim:
1. The compound, (3S,4S)-1-(2,4-dimethoxybenzyl)-4-[(R)-2,2-dimethyl-1,3-dioxolan-4-yl]-3-[(R)-1-hydroxyethyl]-2-azetidinone.
2. The compound, (3S,4S)-1-(t-butyldimethylsilyl)-4-[(R)-2,2-dimethyl-1,3-dioxolan-4-yl]-3-[(R)-1-hydroxyethyl]-2-azetidinone.

* * * * *